United States Patent [19]  [11] 4,252,977
Mitchell et al.  [45] Feb. 24, 1981

[54] NOVEL ACETAMIDE COMPOUNDS AND PROCESS FOR PRODUCING THEM

[75] Inventors: Tyrone D. Mitchell, Albany; Melvin D. Beers, Schenectady, both of N.Y.

[73] Assignee: General Electric Company, Waterford, N.Y.

[21] Appl. No.: 135,958

[22] Filed: Mar. 31, 1980

[51] Int. Cl.$^3$ .................................................. C07F 7/10
[52] U.S. Cl. ................................. 556/411; 260/404.5
[58] Field of Search ...................... 556/411; 260/404.5

[56]  References Cited
U.S. PATENT DOCUMENTS

| 3,417,047 | 12/1968 | Golitz et al. ................. 556/411 X |
| 3,436,415 | 4/1969 | Finkbeiner et al. ............ 556/411 X |
| 3,488,371 | 1/1970 | Klebe ............................... 556/411 |
| 3,776,933 | 12/1973 | Toporcer et al. ................. 556/411 |
| 3,776,934 | 12/1973 | Toporcer et al. ................. 556/411 |
| 4,145,359 | 3/1979 | Homan et al. .................... 556/411 |

Primary Examiner—Paul F. Shaver
Attorney, Agent, or Firm—J. L. Young; E. Philip Koltos; Philip. L. Schlamp

[57]  ABSTRACT

An acetamide compound of the formula,

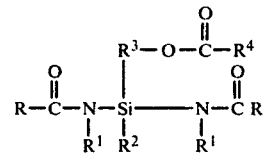

where R, $R^1$, $R^2$, $R^4$ are monovalent hydrocarbon radicals, and $R^3$ is a divalent hydrocarbon radical.

22 Claims, No Drawings

NOVEL ACETAMIDE COMPOUNDS AND PROCESS FOR PRODUCING THEM

BACKGROUND OF THE INVENTION

The present invention relates to novel amidosilane compounds and more particularly the present invention relates to novel silyl-amide compounds which have difunctional amido groups.

Silyl-amide compounds have been developed and patented as can be seen in the disclosure of Klebe, U.S. Pat. No. 3,488,371. Such silyl-amide compounds are also disclosed in Golitz, U.S. Pat. No. 3,417,047 which discloses the use of acetamido functional silanes as cross-linking agents to form one-component room temperature vulcanizable silicone rubber compositions. It was noted in that patent that there had to be at least three acetamido functional groups in the silane for the silane siloxane to function as a cross-linking agent.

Recently in the case of difunctional silyl-amide and siloxanyl amide compounds there has been developed a novel use for such compounds. An example of the disclosure of such silyl-amide compounds is, for instance, to be found in Klebe, U.S. Pat. No. 3,488,371. This patent deals with the synthesis and development of difunctional acetamido and silanes and siloxanes. The disclosures of Toporcer, U.S. Pat. Nos. 3,776,934 and 3,776,933 should be noted in this regard. The U.S. Pat. No. 3,776,934 states that the Klebe patent disclosed dimethyl-bis(N-methyl-acetamido)silanes in methylphenyl-bis(N-methylacetamido)silanes and diphenyl-bis(N-methylacetamido)silanes. It was the alleged invention of this patent to develop methylvinyl-bis(N-methylacetamido)silanes. However, note the disclosure of Klebe, U.S. Pat. No. 3,488,371, which at the bottom of Column 2 and at the top of Column 3 of the patent discloses the purported invention of U.S. Pat. No. 3,776,934.

Irrespective of the above, patents such as U.S. Pat. No. 4,020,044 appreciated the use of, for instance, methylvinylacetamido silanes as chain extenders for silanol-terminated diorganopolysiloxanes. Other patents such as U.S. Pat. No. 3,817,909 disclose the use of the various methylphenyl and methylvinyl and dimethylacetamido functional silanes which are difunctional in the acetamido groups as couplers to form one-component RTV compositions of extremely low modulus.

Briefly, these compositons function as follows: The difunctional acetamido silanes are added to the silanol polymer along with other fillers and additives and once added result in the difunctional acetamido silanes reacting with the silanol groups of linear silanol polymers to remit in acetamido silyl terminal groups. There is also incorporated into such a composition a small amount of aminoxy functional cyclopolysiloxanes as cross-linking agents. The composition is packaged in a single package in a substantially anhydrous state. When it is desired to cure the composition, the composition is exposed to moisture which results in the hydrolysis of the aminoxy groups and cross-linking and coupling to long chain higher molecular weight linear diorganopolymers so as to result in an elastomer. However, because of the high or the long chain polymer resulting from the coupling reaction the composition has an extremely low modulus as exhibited by elongations of 800 to 1,600 percent and a small but appreciable tensile strength. Such compositions have been found to have good unprimed adhesion properties and as such have been found to be useful as sealants.

One purpose of such sealants, for instance, has been to seal the joints in concrete pavement so as to prevent moisture from entering beneath the joint that is formed between the concrete slabs and freezing and expanding thus causing up-heaval of the concrete block.

Accordingly, it was highly desirable to find a more reactive difunctional acetamido coupler that is more reactive than that of most of the prior difunctional acetamido silanes and siloxanes.

In another vein, it is disclosed in Toporcer, U.S. Pat. No. 3,776,933, that the amido silanes can be produced by reacting a dichlorohydridosilane with the appropriate intermediate to produce the diorganodichlorosilane. The resulting diorganodichlorosilane can then be reacted with a metal salt of an organic amide so as to replace the chlorine groups in the dichlorosilane with amide groups and give off an alkaline metal salt as the by-product. The resulting salt can then be filtered off and the solvent removed to result in the desired product in substantial yield. The above process was utilized with advantage to produce the desired difunctional amido silane in substantial yield. Nevertheless, it was undesirable in that it necessitated the handling of an alkali metal solid which is undesirable because it might cause a fire. Accordingly, it was highly desirable to modify this process to produce novel difunctional acetamido silanes which were more reactive than the prior art difunctional acetamido silanes even though the process was not as advantageous as would be desired. In addition, it was highly desirable to modify the prior art processes both utilizing alkali metal and not utilizing an alkali metal to product novel difunctional acetamido silanes which were more reactive than the prior art difunctional acetamido silanes.

Accordingly, it was one object of the present invention to provide novel difunctional acetamido silanes.

It is another object of the present invention to provide a novel process for producing novel difunctional acetamido silane compounds.

It is an additional object of the present invention to provide novel difunctional acetamido silanes which can function as couplers in the production of extremely low modulus one-component RTV systems.

These and other objects of the present invention are accomplished by means of the disclosure set forth hereinbelow.

SUMMARY OF THE INVENTION

In accordance with the above objects of the present invention, there is provided by the present invention an acetamido compound of the formula,

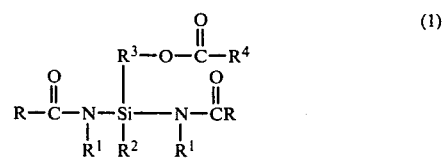

where R, $R^1$, $R^2$, $R^4$ are monovalent hydrocarbon radicals, and $R^3$ is a divalent hydrocarbon radical. Preferably, R, $R^1$, $R^2$, $R^4$ is selected from the class consisting of alkyl radicals of 1 to 8 carbon atoms, mononuclear aryl radicals of up to 8 carbon atoms, alkenyl radicals of 2 to 8 carbon atoms and haloalkyl radicals of 1 to 8 carbon atoms. In the compound of the above Formula (1), $R^2$ is selected from the class of alkyl radicals of 1 to 8 carbon atoms, vinyl, phenyl, and preferably $R^3$ is selected from alkylene and arylene radicals of 2 to 8 carbon atoms. The compound is produced by reacting the appropriate hydrosilane with the desired intermediate in the presence of a platinum catalyst so as to add on the organic intermediate group onto the hydrogen atom of the silane and the corresponding silane is reacted with an organic amide in a solvent to produce the desired amide. More details of the desired process will be given below.

DESCRIPTION OF THE PREFERRED EMBODIMENT

In the foregoing Formula (1), R, $R^1$, $R^2$, $R^4$ can be any monovalent hydrocarbon radical. Examples of such radicals are an alkyl radical of from 1 to 8 carbon atoms such as, methyl, ethyl, etc.; alkenyl radicals such as, vinyl, allyl, etc.; mononuclear aryl radicals such as, phenyl, methylphenyl, ethylphenyl, etc.; cycloalkyl radicals such as, cyclohexyl and cycloheptyl, etc.; and fluoroalkyl radicals such as, 3,3,3-trifluoropropyl. More preferably, the R, $R^1$, $R^4$ is selected from the class of alkyl radicals of 1 to 8 carbon atoms, mononuclear aryl radicals of up to 8 carbon atoms, aryl radicals of 2 to 8 carbon atoms, and haloalkyl radicals of 3 to 8 carbon atoms. The $R^2$ radical is preferably selected from any mononuclear aryl radical, alkyl radicals or alkenyl radicals of 1 to 8 carbon atoms. However, more preferably it is selected from alkyl radicals of 1 to 8 carbon atoms, vinyl and phenyl, and more specifically it is preferably methyl, vinyl or phenyl. The $R^3$ radical can be any linear or branch chained divalent hydrocarbon radical but is more preferably selected from alkylene and arylene radicals of up to 8 carbon atoms such as, methylene and phenylene. Most preferably, in the compound of Formula (1), R, $R^1$, $R^4$ and $R^2$ are methyl and $R^3$ is ethylene.

This is a novel compound which is very reactive as a coupler in forming one-component RTV systems either where the cross-linking agent is a ketoximo functional silane or an aminoxy functional silane. For instance, see the disclosure of the application of M. D. Beers, entitled "Extreme Low Modulus RTV Compositions", Ser. No. 135,959, filed on the same date as the instant case. The acyloxy alkylene groups in the polymer imparts a high reactivity to the amide groups with the acyloxy alkylene group still being a stable entity which is not hydrolyzed off when the difunctional amide silane is mixed with a silanol diorganopolysiloxane polymer and with a ketoxime or aminoxy functional cross-linking agent.

The high reactivity of the difunctional amido groups in such coupler of Formula (1) permits a rapid build-up chain length in the RTV composition without cross-linking of the system. There is incorporated into the composition from 0.1 to 5 parts by weight of a cross-linking agent which can be a ketoxime functional silane or an aminoxy functional silane or siloxane. There also can be incorporated into the composition other various additives such as, flame retardant additives, fillers, heat stabilizing additives and etc. The composition is packaged in a substantially anhydrous state. When it is desired to cure the composition, the package is broken and the composition is exposed to atmospheric moisture. The atmospheric moisture hydrolyzes the ketoxime functional groups or aminoxy functional groups in the polymer mixture as well as the amido functional groups.

This results in the cross-linking of the long polymer chains to form a long chain polymer which is slightly cross-linked such that the composition cures to an elastomer which has extremely high elongation and a low tensile strength, thus resulting in a composition with an extremely low modulus. Thus, by using the compound of Formula (1) as a coupler in the formation of one-component RTV systems, it is possible to form cured one-component RTV systems with a percent elongation in the range of 1,000 to 1,600 percent.

These compositions are novel in themselves as disclosed in the copending patent application of M. D. Beers, Ser. No. 135,959, however, also the amido functional silane with the acyloxyalkyl functional groups is also a novel ingredient as disclosed in the instant patent application. The process for forming such an amido functional silane are various. The process that may be utilized is one similar to that disclosed in Toporcer et al, U.S. Pat. No. 3,776,933. Utilizing such process the compound of Formula (1) may be formed by reacting the silane of the formula,

(2)

with an intermediate of the formula,

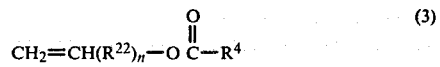

(3)

where $R^2$, $R^4$ are as previously defined, Y is halogen and preferably chlorine to form a compound of the formula,

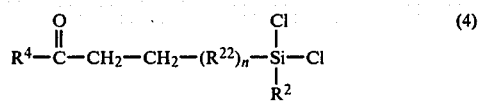

(4)

in the presence of a platinum catalyst where $R^{22}$ is a divalent hydrocarbon radical, R is as previously defined and n is 0 or 1, to form an intermediate, and then taking an intermediate and reacting with an amide of the formula,

(5)

to produce the desired product where R, $R^1$ are as previously defined and M is an alkali metal and is preferably selected from sodium, potassium and lithium. The first reaction of the chlorosilane to the olefin containing organic intermediate is preferably carried out in the presence of a solvent so as to permit intimate contact of the reactants. The platinum catalyst can be present as solid platinum, platinum deposited on charcoal, gamma-alumina, or it can be one of the well-known solubilized platinum catalysts which are well known in the art such as disclosed in Karstedt, U.S. Pat. No. 3,715,334.

The first reaction of the dichlorosilane with the organic intermediate is preferably carried out in a solvent such as one of the aliphatic hydrocarbon solvents, aromatic hydrocarbon solvents or chlorinated hydrocarbon solvents such as xylene, toluene, benzene, heptane, hexane, cyclohexane, methylenechloride and etc.

The reaction is a simple addition reaction and is preferably carried out such as utilizing one mole of the dichlorosilane per mole of the organic compound. It should be noted that $R^{22}$ is preferably an alkylene and arylene radical of up to 6 carbon atoms. In the formula, preferably n is equal to 0. It may be equal to 0 or 1. Preferably, the organic compounds, which are well known to the art, are utilized at a concentration of 1 mole of the organic compound per mole of the dichlorosilane. More preferably, the hydrogenodichlorosilane is utilized at a 10 mole percent excess. This reaction is preferably carried out at atmospheric pressure but may be carried out at subatmospheric or super-atmospheric pressure. The intermediate may be utilized in the second step of the process. It should be noted that this first step of the process may take place at a time period of anywhere from 0.5 hours to 6 hours. It is preferably carried out at anywhere from 25° to 100° C.–more preferably from 25° to 50° C. Temperatures above room temperature may be utilized to speed up the rate of reaction. The organic amide is taken and reacted with sodium metal or an alkali metal in a solvent such as, xylene, toluene, hexane, heptane, so as to yield the metal amide compound so as to obtain the reactant of Formula (4). It should be noted that the hydrogenodichlorosilane of Formula (2), the intermediate of Formula (4) and the amide, as well as the metal amide of Formula (5), are well known compounds. Preferably, the intermediate of the first step of the process is reacted with 2 moles of the metal amide. More preferably, there is utilized a slight excess. If 10 mole percent excess or 20 percent mole excess of the metal amide over 2 moles of the amide per mole of the dichlorosilane intermediate. The reaction may be carried out at atmospheric pressure or super-atmospheric pressure.

In Formula (5) of the amide preferably K is alkali metal and R and $R^1$ can be any monovalent hydrocarbon radical. More preferably, K is sodium and R and $R^1$ can be any monovalent hydrocarbon radical, and can be selected from alkyl radicals of 1 to 8 carbon atoms, vinyl radicals and phenyl radicals. Examples of the metal salt of the organic amide include sodium N-methylacetamide, sodium N-ethylacetamide, sodium N-propylacetamide, sodium N-phenylacetamide, sodium N-methylpropionamide, sodium N-methylbenzamide, sodium N-ethylpropionamide, sodium N-propylpropionamide, sodium N-phenylpropionamide, sodium N-ethylbenzamide, sodium N-propylbenzamide, sodium N-phenylbenzamide, potassium N-methylacetamide, potassium N-ethylacetamide, potassium N-propylacetamide, potassium N-phenylacetamide, potassium N-methylpropionamide, potassium N-methylbenzamide, potassium N-ethylpropionamide, potassium N-propylpropionamide, potassium N-phenylpropionamide, potassium N-ethylbenzamide, potassium N-propylbenzamide, potassium N-phenylbenzamide, lithium N-methylacetamide, lithium N-ethylacetamide, lithium N-propylacetamide, lithium N-phenylacetamide, lithium N-methylpropionamide, lithium N-methylbenzamide, lithium N-ethylpropionamide, lithium N-propylpropionamide, lithium N-phenylpropionamide, lithium N-ethylbenzamide, lithium N-propylbenzamide, and lithium N-phenylbenzamide.

The metal salts of the organic amides are prepared by reacting small particles of the metal with an organic amide in an inert hydrocarbon solvent where preferably the mixture is refluxed during the reaction. The metal amde is purified by evaporating or stripping off a solvent to yield a metal salt of the organic amide and the reactive metal can be reused in other processes so as to react with organic amides to produce the metal salt of the organic amide. It should be noted that the excess metal should be removed from the reaction media prior to the stripping of a solvent due to the danger of fire. The metal salt of the amide of Formula (5) is then taken and reacted with a dichlorosilane intermediate and as stated previously, in a 2:1 mole or proportion. Preferably, the reaction is carried out in the presence of an inert hydrocarbon solvent in which the sodium salt of the halogen that is given off as a by-product is insoluble. Examples of solvents that may be utilized are toluene, benzene, xylene, heptane, hexane, mineral spirits and other mixtures of hydrocarbons and ethers such as, tetrahydrofuran, diethylether and glycol ethers such as, propylene glycol monomethyl ether. The solvent that is utilized is any stable hydrocarbon that can be inert to the reactants of the instant process such that the product of the process is insoluble in the solvent. It is desired that in the instant process the products, as well as the intermediate reactant (but desirably the by-products) not be soluble in the solvent thus allowing the final product to be separated from the by-products with simplicity. This final second reaction desirably takes place in a period of time varying from ½ to 12 hours and more preferably from ½ hour to 6 hours in a temperature of anywhere from 0° to 150° C. More preferably, the temperature of 0° to 100° C. in a period of time varying from ½ hour to 6 hours. To facilitate the process after the metal salt of the amide is in suspension in the organic solvent, the halosilane intermediate can be simply added to the suspension. Preferably, it is added in increments slowly since this allows a more stable reaction transition period. The second reaction as well as the first can be carried out at sub-atmospheric or super-atmospheric pressure but is preferably carried out at atmospheric pressure so as to avoid the use of the pressure equipment. After the reaction is completed, then the by-product salts that are formed may be filtered out or decanted out and the solvent stripped off to give the desired product. Preferably, the desired amide is utilized in solvent form and then the solvent is stripped off to yield the one-component RTV base mixture. The reaction may be determined to be over when the reaction mixture is either basic or neutral indicating either that all the chlorine in the composition has been converted to salts and that the halosilane intermediate reactant has been fully reacted and consumed in the reaction. As long as chlorine or halosilanes are in the reaction, the mixture will have acidic nature.

The second step of the instant process is carried out in one substantial complete absence of moisture so that once the amide groups have been added to the silane they will not be hydrolyzed off by the moisture. If there is moisture present, the amide groups will hydrolyze off the silane of the silicone compound of Formula (1). It should be noted that while this process has the advantage of producing a high yield of the desired product of Formula (1), it nevertheless is undesirable because of the use in the process of an alkali metal which is dangerous since it might accidentally cause a fire. Accordingly, sodium and other alkali metal processes are not preferred generally because of the danger of accidental fire.

A more general and more desirable reaction for producing a compound of Formula (1) is as follows. The first part of the reaction is the same, that is, again the compound of Formula (2) is reacted with the compound of Formula (3) to produce a dihalosilane intermediate and this reaction takes place in the presence of a platinum catalyst, as noted previously, which is preferably present at a concentration of anywhere from 1 to 300 parts per million. This reaction is preferably carried out in a hydrocarbon solvent which may be any of the hydrocarbon solvents mentioned previously, but just to repeat, it is preferably a hydrocarbon solvent such as those disclosed in Klebe, U.S. Pat. No. 3,488,371, such as, benzene, toluene, chloroform, carbon tetrachloride, dioxane, tetrahydrofuran, diethylether, dimethylether, diethylene glycol and etc. Accordingly, the hydrocarbon solvents may also be any organic solvent in which the reactants are soluble.

After the reaction is complete, the excess hydride chlorosilane is stripped off by heating the mixture to above the reflux of the solvent which may be anywhere from 80° to 120° C. to leave behind the intermediae dihalosilane in substantially pure form. The solvent is stripped off to yield the pure intermediate or the material may be utilized in solution form. In the second part of the process, the halosilane intermediate may be reacted with an amide of the formula,

  (6)

to produce the desired product where R and $R^1$ are as previously defined. This reaction has a tertiary amine as a catalyst or a reaction promoter. The tertiary amine has the formula,

where $R^{23}$ is a monovalent hydrocarbon radical, more preferably, selected from an alkyl radical of 1 to 8 carbon atoms and a phenyl. Illustration of tertiary amine which can be employed in the process of the present invention are those having a dissociation constant in the order of at least $1 \times 10^{-6}$-for example, triethylamine, trimethylamine, phenyldimethylamine, tributylamine, tripropylamine, triphenylamine, N-methylpyrrolidine, methyldiethylamine, benzylpyrrolidine, dimethylethylamine, and etc.

This reaction utilizes one of the hydrocarbon solvents disclosed above as a solvent for the first part of the reaction, as stated previously, in which the dihalosilane intermediate is dissolved at the end of the reaction. It should be noted that in the first step of the process which is the same as the previous process, a solvent does not have to be used. A solvent is preferably utilized and one of the solvents mentioned above. Then the solution of the intermediate can be utilized by simply adding to the reaction mixture the tertiary amine, then adding the amide in the appropriate proportion. As stated in Klebe, U.S. Pat. No. 3,488,371, there may be utilized anywhere from 1 mole of the tertiary amine for each mole of the amide employed for the reaction. Smaller amounts can be utilized, however, if smaller amounts of tertiary amine are utilized then there is free hydrogen halide present in the reaction which leads to undesired by-products. Generally, it is preferred to employ two moles of the tertiary amine for each mole of the halosilane so as to use up or tie up all the hydrogen halide that is given up as a result of the reaction. Accordingly, the second step of the reaction of this alternate preferred process is that there must be present a hydrocarbon solvent and preferably one of the hydrocarbon solvents disclosed. However, one of the difficulties with this second preferred process in the past is that there be formed amide products which would be somewhat soluble in the solvent and would not be easily removable from the final product of Formula (1) by standard means. Accordingly, it was found out when it was attempted to remove the amide by-products in solution with the product of Formula (1), the amide by-products would react with the final product in solution so as to cause reversion. Accordingly, it was highly desirable to improve the process by removing amine by-products that were formed in the second reaction of the preferred process of the instant case.

Accordingly, in one preferred embodiment of the instant case, the second reaction is carried out in a mixture of organic solvents, thus there is preferably utilized a mixture of an aromatic solvent with an aliphatic hydrocarbon solvent, both of which solvents are inert such that the amine by-products will precipitate from the solvent solution but the solvent will retain in solution the product of Formula (1). The aromatic solvents are xylene, toluene, benzene and are utilized at a concentration of anywhere from 20% by volume up to 80% by volume with 10% to 20% by volume of an aliphatic hydrocarbon solvent mixed in the solvent mixture which aliphatic hydrocarbon solvent is preferably selected from hexane, cyclohexane, pentane, heptane, octane, nonane, and so forth. If the dihaloorganosilane intermediate is prepared in solvent solution, then there is simply added a cosolvent in the above solvent concentrations and more preferably at a solvent concentration of 40 to 60 mole percent by volume of the aromatic solvent and the rest of the solvent in the solution is an aliphatic hydrocarbon solvent. The tertiary amine is added in the mole proportion as stated previously and then finally there is added the amide preferably slowly with agitation. Accordingly, in a period of time varying from 0.5 to 12 hours, more preferably varying from 0.5 to 6 hours, there is obtained the desired product of Formula (1). The undesired amines and a substantial amount of the undesirable amide by-products are precipitated out. Preferably, the process is carried out at temperatures of 0° to 20° C., or more preferably at a temperature varying from 0° to 10° C. so as to increase the yield and decrease the formation of undesired by-products. The process can be carried out at atmospheric pressure, super-atmospheric pressure, or sub-atmospheric pressure. It is preferably carried out at atmospheric pressure.

After the reaction has gone to completion, which is again evidenced by the reaction media amine being neutral or basic, showing the entire absence of halosilanes, as much of the precipitated by-products are removed and then the solvent is stripped off to give the desired by-products in substantially pure form. The solvent is then removed by heating the reaction mixture or solution to the reflux temperature of the solvent which may be anywhere from the temperature of 80° to 130° C. It should be noted that the product of Formula (1) may be utilized in preparing one-component RTV systems in solvent solution after the undesirable by-products have been removed. Thus, after the undesirable amine by-products and hydrogen have been removed, the product of Formula (1) solution may be taken and added to the base silanol end-stopped polymer as disclosed in docket 60SI-70, and mixed with the polymer and the solvent to be stripped off. It should be noted that this stripping procedure of the solvent, as well as the process for preparing the product of Formula (1) in the second reaction, is preferably carried out in an anhydrous state or substantially anhydrous state so that the amido silane will not hydrolyze its amide groups. It should be noted that along with the mole proportions as disclosed above for the tertiary amine to dihalosilane intermediate there should be utilized at least two moles of the organic amide per mole of the dihalosilane intermediate in the second reaction. More preferably, there is utilized at least 5 to 10 mole percent excess over the stoichiometric amount of the organic amide per mole of the dihalosilane intermediate which is utilized in the preferred process of the instant case. Most preferably, there is a 5% excess; too much excess amide causes side reactions and a loss of coupling efficiency of the product. Once the compound of Formula (1) has been synthesized, it can be mixed with a base silanol end-stopped polymer and then to this base mixture there can be equally added any reinforced or extending filler.

One of the advantages of the amide couplers of the instant case is that they will allow a low viscosity uncured composition to be prepared and yet the composition will cure to a silicone elastomer of high elongation. Various types of fillers may be added to the composition such as reinforcing, semi-reinforcing and extending fillers to give the composition a variety of properties. The composition is packaged in the substantially anhydrous state in a one-component package and when it is desired to cure the composition, the package is simply broken and the composition applied and exposed to atmospheric moisture. Upon being exposed to atmospheric moisture, the cross-linking agent hydrolyzes as well as the amide groups that are still present in chain-terminated positions so as to result in cross-linking of the long polymer chains. As a result, the compound will then form a skin in as little as 10 minutes to 60 minutes and fully cure to a silicone elastomer in periods of time of 24 hours to 3 days. As a result of a utilization of a coupler in the instant invention in such one-component RTV systems, there results a composition with low viscosity in the uncured state but with elongation in the range of 800 to 1600 percent in the cured elastomeric state with good adhesion to various types of substrates.

The examples below are given for the purpose of illustrating the present invention and are not given for the purpose of setting limits and boundaries to the invention of the instant case. All parts are by weight.

EXAMPLE 1

To a reaction vessel was charged 475 parts of toluene followed by 54.4 parts of N-methylacetamide. This mixture was stirred and refluxed to remove final traces of water by azeotropic distillation. The toluene level was adjusted to compensate for any toluene removed during the drying process. After this step, the solution was cooled to less than 20° C. (preferably 8°–10° C.) and there was added 77.4 parts of dry triethylamine. From a dropping funnel was added 73.4 parts of (2-acetoxyethyl)methyldichlorosilane at such a rate that the temperature did not rise above 25° C., preferably within 5° C. of the initial temperature. When the addition was completed, the reaction mixture was stirred for 30 minutes followed by heating at 100° C. for 4 hours. Because of the large amount of salts present in the reaction mixture, vigorous agitation continued throughout the entire process. After heating, the reaction mixture was cooled to less than 20° C. and filtered to remove the salts. The filtrate was returned to a clean vessel and the solvent removed under vacuum (70° C./20 mm). When no more solvent distilled, the residue was cooled and filtered through Celite. The yield was 84 parts (85%).

When the residue was mixed with a silanol end-stopped poly(dimethylsiloxane) (0.09% silanol) in a mole ratio ranging from 1:1 up to 4:1, the viscosity of the polymer increased from 3,000 centistokes to over 500,000 centistokes in one hour. This test illustrates the effectiveness of the product, (2-acetoxyethyl)methyl bis(N-methylacetamido)silane, in coupling silanol polymer to high molecular weight.

EXAMPLE 2

The reaction was carried out in the same manner as was Example 1, except a mixture of 250 parts of heptane and 250 parts of toluene was used as solvent. This solvent mixture was effective in removing unreacted N-methylacetamide because of its insolubility in the solvent mixture. The product obtained was a clear, straw-colored liquid. The toluene-heptane mixture had to be used since the product was completely insoluble in heptane. The yield of product from this reaction was from 60–80%.

EXAMPLE 3

In a reaction similar to Example 1, tri-n-butylamine was used instead of triethylamine. When the reactants were mixed no evidence of reaction was observed even after vigorous reflux at 110° C. Analysis of the reaction mixture by gas chromatography showed the reactants to be present unchanged. This example vividly illustrates that the reaction is not only controlled by amine basicity but also by steric factors. Tri-n-butylamine is as basic as triethylamine but the bulky butyl group probably interferes with its function as an HCl acceptor in this system.

EXAMPLE 4

In a reaction similar to Example 1, pyridine was used instead of triethylamine. When the reactants were mixed, no evidence of reaction was observed even after vigorous reflux at 110° C. Analysis of the reaction mixture by gas chromatography showed the reactants to be present unchanged. Thus pyridine was not basic enough to function as an effective HCl acceptor in this system.

We claim:

1. An acetamide compound of the formula,

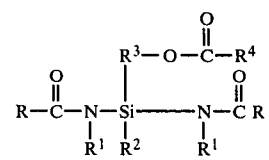

where R, $R^1$, $R^2$, $R^4$ are monovalent hydrocarbon radicals, and $R^3$ is a divalent hydrocarbon radical.

2. The compound of claim 1, wherein R, $R^1$, $R^4$ is selected from the claims consisting of alkyl radicals of 1 to 8 carbon atoms, mononuclear aryl radicals of up to 8 carbon atoms, alkenyl radicals of 2 to 8 carbon atoms and haloalkyl radicals of 3 to 8 carbon atoms.

3. The compound of claim 1, wherein $R^2$ is selected from the class consisting of alkyl radicals of 1 to 8 carbon atoms, vinyl and phenyl.

4. The compound of claim 1, wherein R and $R^1$, and $R^4$ are methyl.

5. The compound of claim 1, wherein $R^3$ is selected from the class consisting of alkylene and arylene radicals of 2 to 8 carbon atoms.

6. The compound of claim 1, in which R, $R^1$, $R^4$ and $R^2$ are methyl and $R^3$ is ethylene.

7. The process for forming an acetamide compound of the formula,

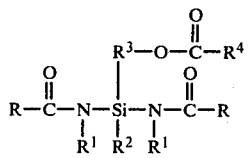

where R, $R^1$, $R^2$, $R^4$ are monovalent hydrocarbon radicals and $R^3$ is a divalent hydrocarbon radical, comprising (1) reacting a silane of the formula,

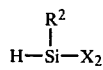

where $R^2$ is as previously defined, X is halogen with a compound of the formula,

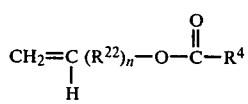

in the presence of a platinum catalyst where $R^{22}$ is a divalent hydrocarbon radical and $R^4$ is as previously defined to form an intermediate, and (2) taking the intermediate and reacting it with an amide of the formula,

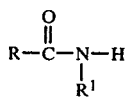

to produce the desired product, where R, $R^1$ are as previously defined.

8. The process of claim 6, wherein step (1) takes place at a temperature of 25° to 100° C., at atmospheric pressure and wherein the compounds are reacted at a 1:1 mole ratio.

9. The process of claim 6, wherein in step (1), after the reaction is completed in a time period varying from 0.5 to 6 hours, the silane product is purified by distillation.

10. The process of claim 6, wherein in step (2) there is utilized as a reaction promoter a tertiary amine of the formula, $$R_3^{23} N$$

where $R^{23}$ is a monovalent hydrocarbon radical.

11. The process of claim 10, wherein the reaction in step (2) takes place in a stable organic solvent.

12. The process of claim 10, wherein the stable organic solvent is selected from the class consisting of toluene, benzene, xylene, pentane, heptane, hexane, mineral spirits, and ether solvents.

13. The process of claim 12, wherein step (2) takes place at a temperature of 0°-20° C. for 0.5 to 12 hours under vacuum.

14. The process of claim 12, wherein after reaction in step (2) is complete the precipitate that is formed is filtered out and then the solvent is distilled off to give the desired product.

15. The process for forming an acetamide compound of the formula,

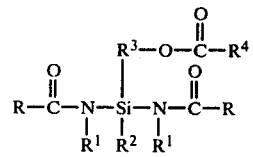

where R, $R^1$, $R^2$, $R^4$ are monovalent hydrocarbon radicals and $R^3$ is a divalent hydrocarbon radical comprising (1) reacting a silane of the formula,

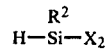

where $R^2$ is as previously defined, X is halogen with a compound of the formula,

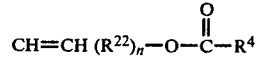

in the presence of a platinum catalyst where $R^{22}$ is a divalent hydrocarbon radical, n is 0 or 1 and R is as previously defined to form an intermediate and (2) taking the intermediate and reacting it with an amide of the formula,

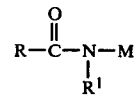

to produce the desired product where R, $R^1$ are previously defined, M is an alkali metal.

16. The process of claim 15, wherein step (1) takes place at a temperature of 0° to 150° C. at atmospheric pressure and wherein the compounds are reacted at a 1:1 mole ratio.

17. The process of claim 15, wherein in step (1) after the reaction is completed in a time period varying from 0.5 to 6 hours, the silane product is purified by distillation.

18. The process of claim 17, wherein in step (2) there is utilized a reaction promoter which is a tertiary amine of the formula, $$R_3^{23} N$$

where $R^{23}$ is a monovalent hydrocarbon radical.

19. The process of claim 17, wherein the reaction in step (2) takes place in a stable organic solvent.

20. The process of claim 18, wherein the stable organic solvent is selected from the class consisting of toluene, benzene, xylene, pentane, hexane, heptane, mineral spirits and ether solvents.

21. The process of claim 11 wherein step (2) is carried at a temperature of 0° to 20° C. for 0.5 to 12 hours under vacuum.

22. The process of claim 20, wherein after step (2) is complete the precipitates are filtered out and the solvent is distilled off to give the desired product.

* * * * *